US012139072B2

(12) United States Patent
Stent et al.

(10) Patent No.: US 12,139,072 B2
(45) Date of Patent: Nov. 12, 2024

(54) VEHICULAR WARNING SYSTEM AND METHOD BASED ON GAZE ABNORMALITY

(71) Applicant: Toyota Research Institute, Inc., Los Altos, CA (US)

(72) Inventors: Simon A.I. Stent, Cambridge, MA (US); Heishiro Toyoda, Mountain View, CA (US)

(73) Assignee: Toyota Research Institute, Inc., Los Altos, CA (US)

(*) Notice: Subject to any disclaimer, the term of this patent is extended or adjusted under 35 U.S.C. 154(b) by 244 days.

(21) Appl. No.: 17/690,664

(22) Filed: Mar. 9, 2022

(65) Prior Publication Data

US 2023/0286437 A1 Sep. 14, 2023

(51) Int. Cl.

| | |
|---|---|
| ***B60Q 9/00*** | (2006.01) |
| ***G06T 7/00*** | (2017.01) |
| ***G06T 7/70*** | (2017.01) |

(52) U.S. Cl.

CPC ............ *B60Q 9/008* (2013.01); *G06T 7/0012* (2013.01); *G06T 7/70* (2017.01); *G06T 2207/30041* (2013.01); *G06T 2207/30268* (2013.01)

(58) Field of Classification Search

CPC ............... A47L 11/283; A47L 11/4008; A47L 11/4013; A47L 11/4044; A47L 11/4055; A47L 11/4061; A47L 11/4083; G06Q 10/20; G06Q 30/0633; H04Q 9/00; H04Q 2209/43; H04Q 2209/823

See application file for complete search history.

(56) References Cited

U.S. PATENT DOCUMENTS

| | | | | |
|---|---|---|---|---|
| 10,866,635 | B2 | 12/2020 | Stent | |
| 2015/0116197 | A1* | 4/2015 | Hamelink | G09G 3/003 345/156 |
| 2019/0367050 | A1* | 12/2019 | Victor | G06V 20/597 |
| 2021/0113079 | A1 | 4/2021 | Tomasi et al. | |
| 2021/0383566 | A1* | 12/2021 | Matsumoto | G06V 40/18 |
| 2022/0011132 | A1* | 1/2022 | Jia | G06N 20/00 |

OTHER PUBLICATIONS

Kerr, R. et al., "A Real-Time Lazy Eye Correction Method for Low Cost Webcams", Procedia Computer Science, 2019, vol. 159, pp. 281-290.

* cited by examiner

*Primary Examiner* — Sisay Yacob

(74) *Attorney, Agent, or Firm* — Christopher G. Darrow; Darrow Mustafa PC

(57) ABSTRACT

A vehicular warning system control system can include a processor and a memory in communication with the processor. The memory can include a warning system control module having instructions that, when executed by the processor, cause the processor to detect, using sensor data having information about a gaze of each eye of a driver of a vehicle, an abnormality of a gaze of the driver. The instructions further cause the processor to modify, using the sensor data, a signal emitted by the vehicle when the abnormality is detected.

17 Claims, 7 Drawing Sheets

VEHICULAR WARNING SYSTEM AND METHOD BASED ON GAZE ABNORMALITY

TECHNICAL FIELD

The subject matter described herein relates, in general, to systems and methods for a warning system of a vehicle and, more specifically, to methods for displaying warnings within a vehicle based on a gaze of a driver of the vehicle.

BACKGROUND

The background description provided is to present the context of the disclosure generally. Work of the inventor, to the extent it may be described in this background section, and aspects of the description that may not otherwise qualify as prior art at the time of filing, are neither expressly nor impliedly admitted as prior art against the present technology.

Some current vehicles have gaze detection systems configured to detect a gaze of a driver of the vehicle. Such systems can include various sensors, including cameras, located in the cabin of the vehicle, and directed toward the driver's eyes. In some instances, these gaze detection systems can determine the direction of the driver's gaze and/or identify objects inside the vehicle or outside of the vehicle that the driver is looking toward.

Some current vehicles also include warning systems that may be configured to provide a driver of the vehicle with visual, audial, or haptic warnings to improve the safety of operating the vehicle. Various examples of warning systems include lane departure warning systems configured to warn the driver if the vehicle is near a lane marker or departing a lane, pre-collision warning systems configured to warn the driver of an imminent collision with another vehicle or an obstacle, and blind spot warning systems configured to warn the driver of another vehicle or object located in a blind spot.

SUMMARY

This section generally summarizes the disclosure and is not a comprehensive explanation of its full scope or all its features.

In one embodiment, a system includes a processor and a memory in communication with the processor. The memory has a warning system module having instructions that, when executed by the processor, cause the processor to detect, using sensor data having information about a gaze of each eye of a driver of a vehicle, an abnormality of a gaze of the driver. The instructions further cause the processor to modify, using the sensor data, a signal emitted by the vehicle when the abnormality is detected.

In another embodiment, a method includes the step of detecting, using a processor including sensor data having information about a gaze of each eye of a driver of a vehicle, an abnormality of a gaze of the driver. The method further includes the step of modifying, using the processor, a signal emitted by the vehicle when the abnormality is detected.

In yet another embodiment, a non-transitory computer-readable medium includes instructions that, when executed by a processor, cause the processor to detect, using sensor data having information about a gaze of each eye of a driver of a vehicle, an abnormality of a gaze of the driver. The instructions further cause the processor to modify, using the sensor data, a signal emitted by the vehicle when the abnormality is detected.

Further areas of applicability and various methods of enhancing the disclosed technology will become apparent from the description provided. The description and specific examples in this summary are intended for illustration only and are not intended to limit the scope of the present disclosure.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Described herein is a warning system control system for a vehicle. The vehicle can include a warning system configured to display warnings to a driver of the vehicle, for example, a pre-collision warning, a lane departure warning, and/or a blind spot warning. The vehicle can also include a sensor system configured to detect the gaze of each eye of the driver and detect an abnormality of the gaze of the driver. The abnormality can be, for example, amblyopia, strabismus, a loss of depth perception, an optical prosthesis, or any other abnormality of the eyes. When an abnormality is detected, the warning system control system can be configured to modify a warning displayed by the vehicle. For example, the warning system control system can reposition a warning displayed by the vehicle and/or increase the sensitivity of the warning. This may improve the safety and operation of the vehicle by improving the driver's vision of various signals displayed by the vehicle.

Figure 1:
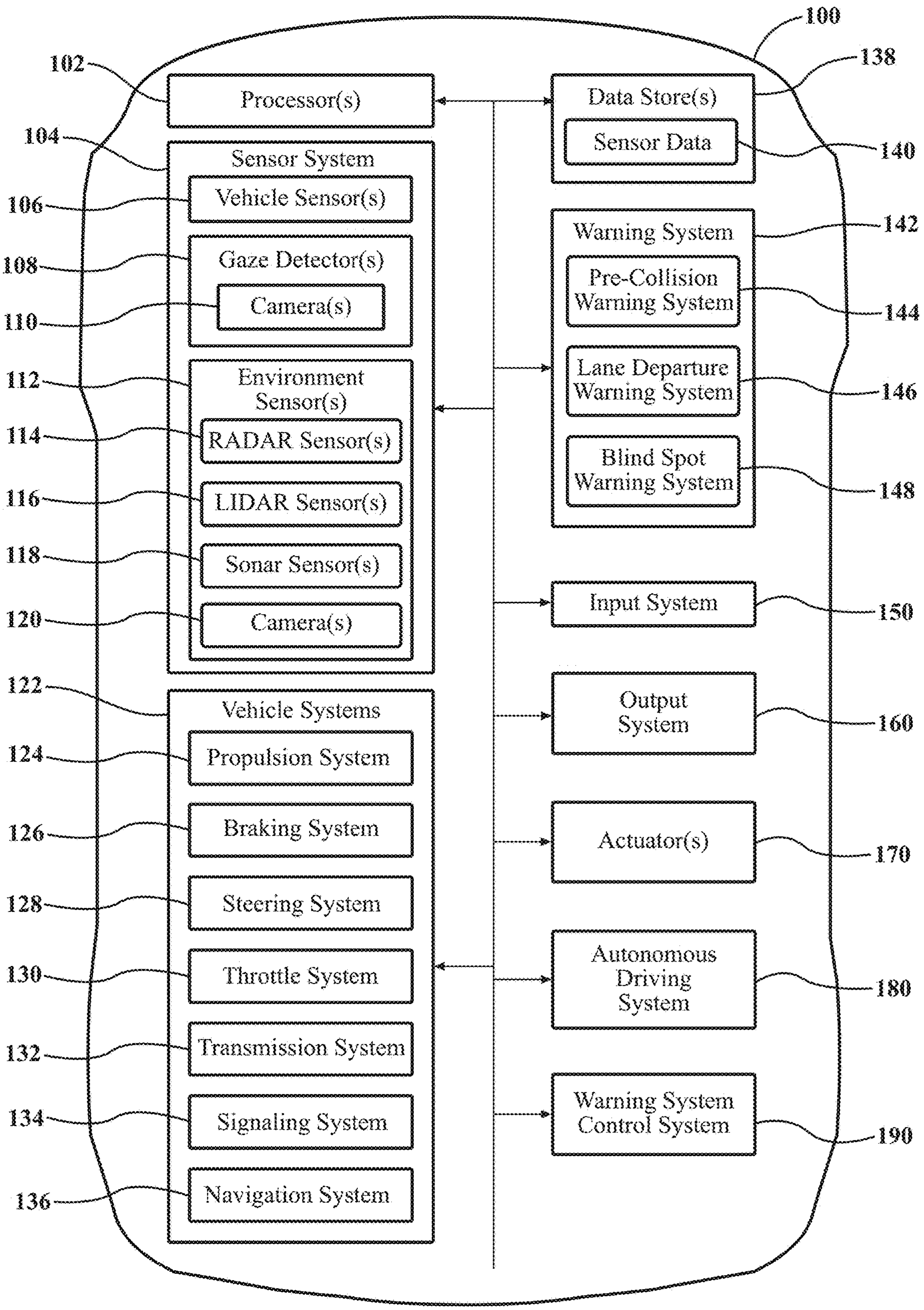
FIG. 1 illustrates one embodiment of a vehicle having a warning system control system.

Referring to FIG. 1, an example of a vehicle 100 is illustrated. As used herein, a "vehicle" is any form of powered transport. In one or more implementations, the vehicle 100 is an automobile. While arrangements will be described herein with respect to automobiles, it will be understood that embodiments are not limited to automobiles. In some implementations, the vehicle 100 may be any robotic device or form of powered transport that, for example, includes one or more automated or autonomous systems, and thus benefits from the functionality discussed herein.

In various embodiments, the automated/autonomous systems or combination of systems may vary. For example, in one aspect, the automated system is a system that provides autonomous control of the vehicle according to one or more levels of automation, such as the levels defined by the Society of Automotive Engineers (SAE) (e.g., levels 0-5). As such, the autonomous system may provide semi-autonomous control or fully autonomous control, as discussed in relation to the autonomous driving system 180.

The vehicle 100 also includes various elements. It will be understood that in various embodiments it may not be necessary for the vehicle 100 to have all of the elements shown in FIG. 1. The vehicle 100 can have any combination of the various elements shown in FIG. 1. Further, the vehicle 100 can have additional elements to those shown in FIG. 1. In some arrangements, the vehicle 100 may be implemented without one or more of the elements shown in FIG. 1. While the various elements are shown as being located within the vehicle 100 in FIG. 1, it will be understood that one or more of these elements can be located external to the vehicle 100. Further, the elements shown may be physically separated by large distances and provided as remote services (e.g., cloud-computing services).

Some of the possible elements of the vehicle 100 are shown in FIG. 1 and will be described along with subsequent figures. However, a description of many of the elements in FIG. 1 will be provided after the discussion of FIGS. 2-7 for purposes of brevity of this description. Additionally, it will be appreciated that for simplicity and clarity of illustration, where appropriate, reference numerals have been repeated among the different figures to indicate corresponding or analogous elements. In addition, the discussion outlines numerous specific details to provide a thorough understanding of the embodiments described herein. It should be understood that the embodiments described herein may be practiced using various combinations of these elements.

Figure 2:
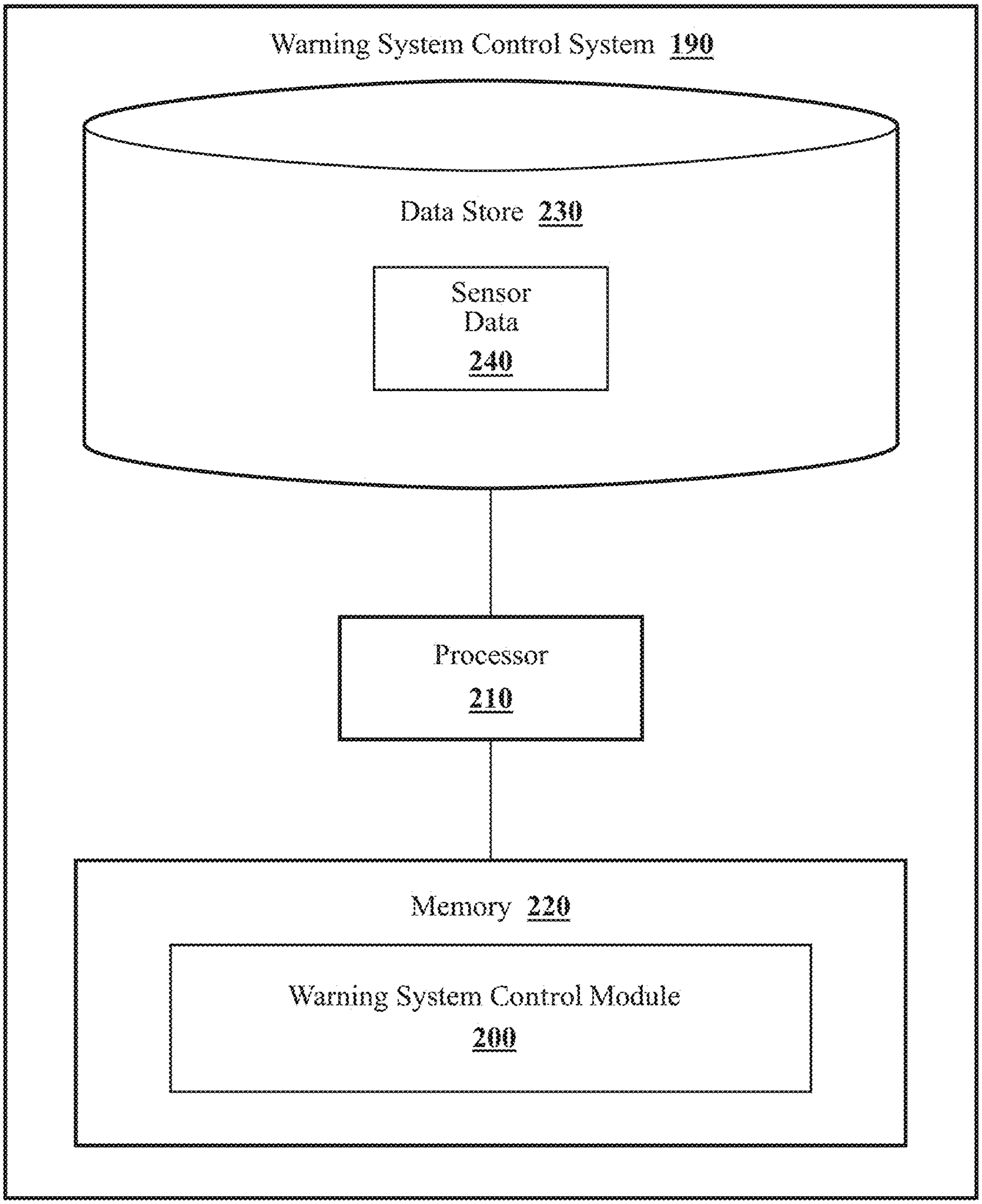
FIG. 2 illustrates an example of a warning system control system that is associated with the vehicle of FIG. 1.

In either case, the vehicle 100 includes a warning system control system 190. The warning system control system 190 may be incorporated within the autonomous driving system 180 or may be separate as shown. With reference to FIG. 2, one embodiment of the warning system control system 190 is further illustrated. As shown, the warning system control system 190 includes a warning system control module 200 and a processor 210. The processor 210 may be a part of the warning system control system 190 or the warning system control system 190 may access the processor 210 through a data bus or another communication path. For example, the processor 210 may be the processor(s) 102 of the vehicle 100. In one or more embodiments, the processor 210 is an application-specific integrated circuit that is configured to implement functions associated with a warning system control module 200. In general, the processor 210 is an electronic processor such as a microprocessor that is capable of performing various functions as described herein. In one embodiment, the warning system control system 190 includes a memory 220 that stores the warning system control module 200. The memory 220 is a random-access memory (RAM), read-only memory (ROM), a hard disk drive, a flash memory, or other suitable memory for storing the warning system control module 200. The warning system control module 200 includes, for example, computer-readable instructions that, when executed by the processor 210, cause the processor 210 to perform the various functions disclosed herein.

Furthermore, in one embodiment, the warning system control system 190 includes a data store 230. The data store 230 is, in one embodiment, an electronic data structure such as a database that is stored in the memory 220 or another memory and that is configured with routines that can be executed by the processor 210 for analyzing stored data, providing stored data, organizing stored data, and so on. Thus, in one embodiment, the data store 230 stores data used by the warning system control module 200 in executing various functions. In one embodiment, the data store 230 includes sensor data 240, along with, for example, other information that is used by the warning system control module 200. The sensor data 240 may include some or all of the sensor data 140 stored in the one or more data store(s) 138 shown in FIG. 1 and described later in this disclosure. Additionally, the data store 230 and the one or more data store(s) 138 of FIG. 1 may be the same data store or may be separate.

Figure 3A:
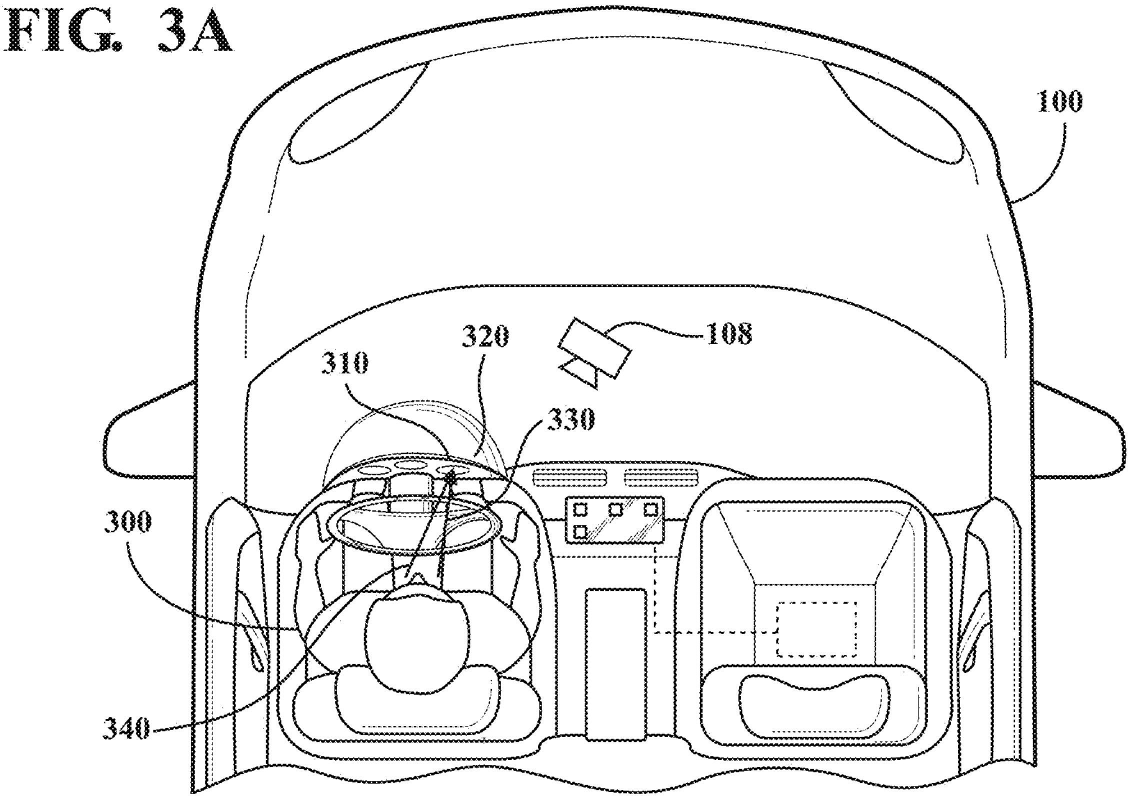
FIG. 3A illustrates an example of a normal gaze of a driver of the vehicle.
Figure 3B:
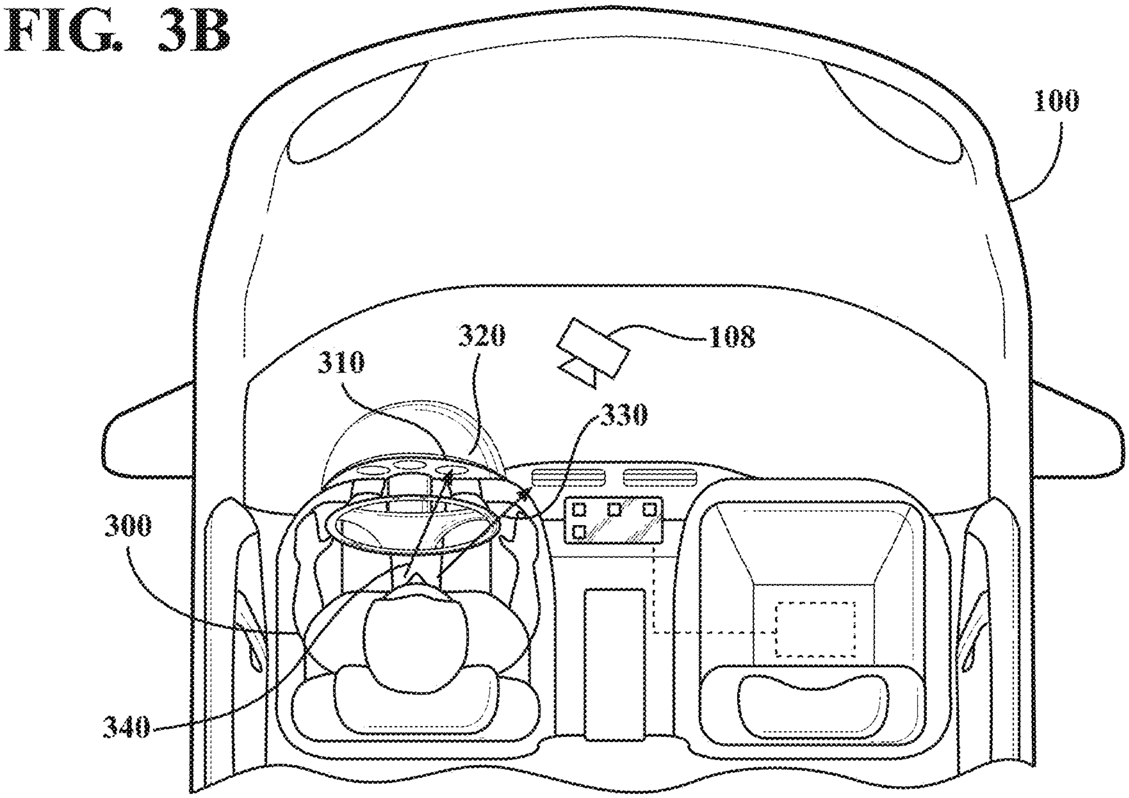
FIG. 3B illustrates an example of abnormal gaze of a driver of the vehicle.

The warning system control module 200 includes instructions that function to control the processor 210 to collect and/or receive sensor data 240. The sensor data 240 can be, for example, sensor data from a sensor system 104 (FIG. 1) of a vehicle 100. Referring to FIGS. 3A and 3B, the sensor data 240 can include information, from one or more gaze detector(s) 108 located within the cabin of the vehicle 100, about a gaze of each eye of a driver 300 of the vehicle 100. Using the sensor data 240, the processor 210 can detect an abnormality of a gaze of the driver 300. The abnormality may be amblyopia ("lazy eye"), strabismus (crossed eyes), a loss of depth perception, an optical prosthesis, or any other type of abnormality of the eyes, such as a diverging gaze or a converging gaze.

The abnormality can be detected in any suitable manner. For example, the vehicle 100 can include a target 310 located in the vehicle 100 in view of the driver 300. The target 310 can be a known position relative to the gaze detector(s) 108 that may include one or more cameras(s) 110 positioned to capture images of the driver's eyes. Images captured by the more cameras(s) 110 may be stored as the sensor data 240. For example, the target 310 can be a location and/or an image displayed on a dashboard 320 of the vehicle or any other suitable target. The gaze detector(s) 108 can be configured to collect sensor data 240 regarding a right eye gaze 330 of the driver and sensor data 240 regarding a left eye gaze 340 of the driver. As mentioned before, the sensor data 240 can include images that include the eyes of the driver 300.

The right eye gaze 330 corresponds to the gaze of a right eye of the driver 300 and the left eye gaze 340 corresponds to the left eye gaze of the driver 300. The sensor data 140 can include information about the right eye gaze 330 and/or the left eye gaze 340 relative to the target 310. The processor 210 can compare the sensor data 240 related to the right eye gaze 330 to the sensor data 240 related to the left eye gaze 340 of the driver 300 and detect an abnormality based on the comparison. In some instances, the processor 210 may be configured to determine the gaze of the driver 300 without the use of a target 310.

For example, as mentioned previously, the sensor data 240 may include images of the eyes of the driver 300. The processor 210 can be configured to analyze these images to analyze the relative positions of different components of each eye of the driver, such as the pupil, sclera, and iris. Based on these relative positions of different components of each eye, the processor 210 can determine the driver's gaze and if any abnormality in the driver's gaze exists, such as amblyopia, strabismus, a loss of depth perception, and/or an optical prosthesis. In the example shown in FIG. 3A, right eye gaze 330 and the left eye gaze 340 is properly focused on the target 310, and therefore, no abnormality is present. However, in the example shown in FIG. 3B, the left eye gaze 340 is focused on the target 310, while the right eye gaze 330 is focused elsewhere. In this example, an abnormality is present. It will be appreciated that the above-described methods for determining the gaze of the driver 300 are not the only methods that can be used. Additional examples of methods for determining gaze can include any of those disclosed in U.S. Pat. No. 10,866,635, which is incorporated herein by reference in its entirety.

Moreover, the warning system control module 200 may include instructions that function to control the processor 210 to determine, based on the sensor data 140 regarding the right eye gaze 330 of the driver 300 and the left eye gaze 340 of the driver, a dominant eye of the driver 300. In some instances, an abnormality of the eyes may lead to one dominant eye and one non-dominant eye, and the driver's brain may suppress signals received by the non-dominant eye. Accordingly, it may be advantageous to determine if the driver 300 has a dominant eye and, if so, which eye is the dominant eye. Using the sensor data 140, the processor 210 may be configured to determine if the right eye or the left eye of the driver 300 is the dominant eye. In the example shown in FIG. 3B, the left eye gaze 340 is focused on the target 310, while the right eye gaze 330 is focused elsewhere. Here, the processor 210 may determine that the left eye is the dominant eye.

The warning system control module 200 further includes instructions that function to control the processor 210 to modify, using the sensor data 240, a signal emitted by the vehicle 100 when the abnormality is detected. The signal can be any signal emitted by the vehicle 100. For example, the signal can be a pre-collision warning, a lane departure warning, a blind spot warning, and/or any other type of signal and/or warning that may be emitted by the vehicle 100. In some instances, modification of the signal may include increasing, by the processor 210, a sensitivity of the warning system that emits the signal. For example, the processor 210 may increase the sensitivity of a pre-collision warning system 144 and/or a lane departure warning system 146 (both shown in FIG. 1) of the vehicle 100.

In such instances, the sensitivity can be a distance threshold, and increasing the sensitivity can include increasing the distance threshold. This will be described in further detail below in connection with FIGS. 4A-5B. Additionally or alternatively, modification of the signal may include repositioning, by the processor 210, the signal displayed by the vehicle 100. For example, the processor 210 may reposition a signal displayed by a blind spot warning system 148 (FIG. 1). This will be described in further detail below in connection with FIGS. 6A and 6B. "Reposition" and "repositioning," as used herein, may include changing the location of the signal displayed by the vehicle 100 and/or displaying the signal in multiple locations on and/or within the vehicle 100. The pre-collision warning system 144, the lane departure warning system 146, and the blind spot warning system 148 will be described in further detail below in connection with FIG. 1.

Figure 4A:
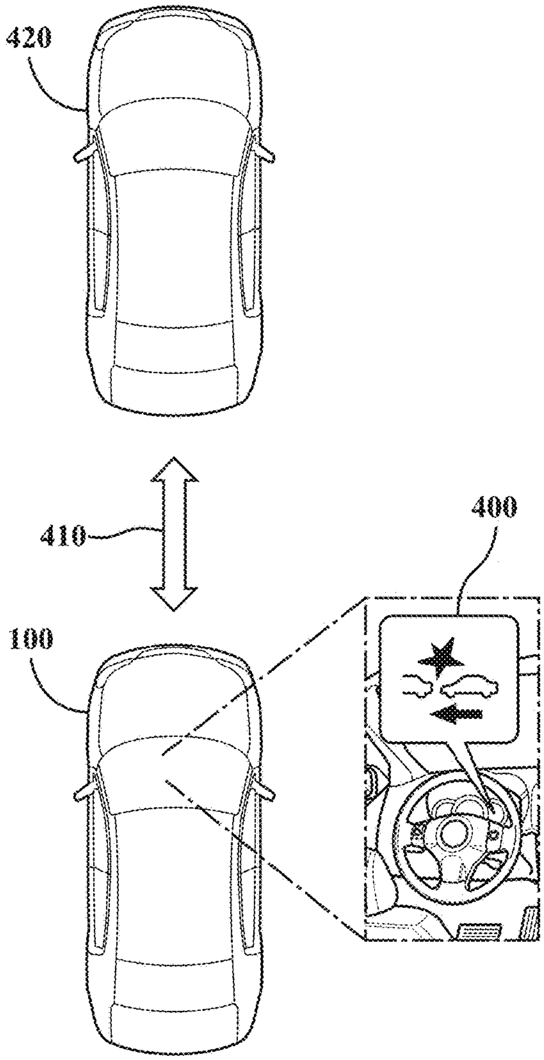
FIGS. 4A and 4B illustrate an example of modifying a pre-collision warning signal displayed by a vehicle based on a detected gaze of a driver of the vehicle.
Figure 4B:
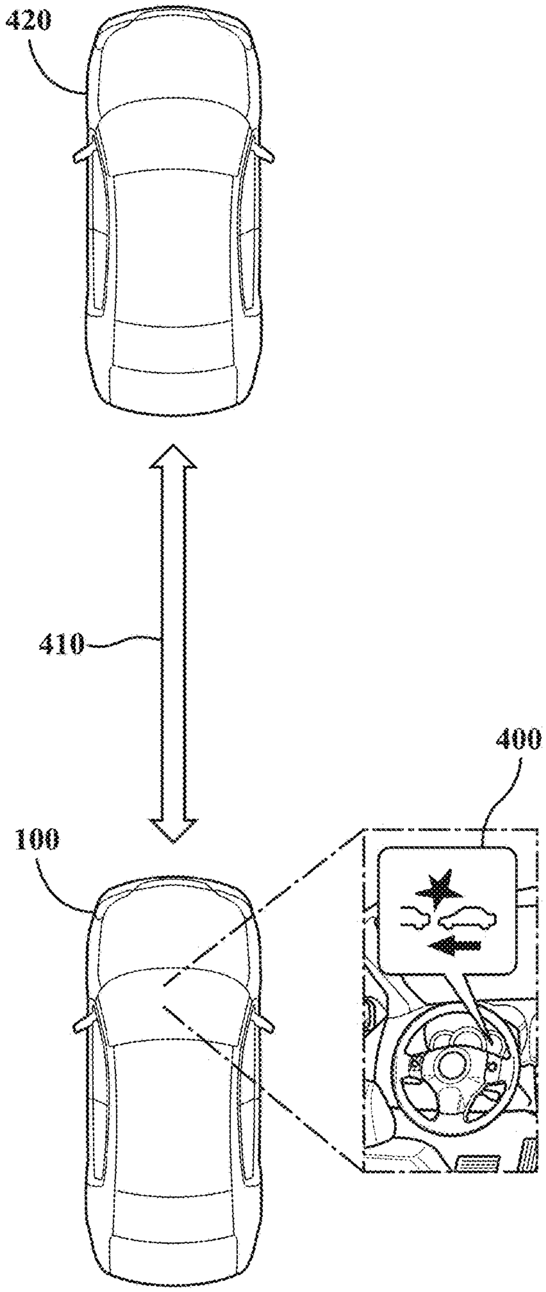

Referring now to FIGS. 4A and 4B, the warning system control module 200 may include instructions that function to control the processor 210 to modify a pre-collision warning 400 emitted by the vehicle 100, as mentioned above. In some instances, the abnormality of the gaze of the driver 300 may cause a loss of depth perception, as described above. In such instances, it may be advantageous to warn the driver 300 of an imminent collision with a preceding vehicle 420 much earlier than would otherwise be needed for a driver with a normal gaze. FIG. 4A illustrates an example of a pre-collision warning 400 for a driver with a normal gaze. The pre-collision warning system 144 may define a distance threshold 410 to the preceding vehicle 420 that may trigger activation of the pre-collision warning 400. FIG. 4B illustrates an example of a pre-collision warning 400 for a driver with an abnormal gaze. As shown, the distance threshold 410 to the preceding vehicle 420 has been increased to accommodate a driver's loss of depth perception.

Figure 5A:
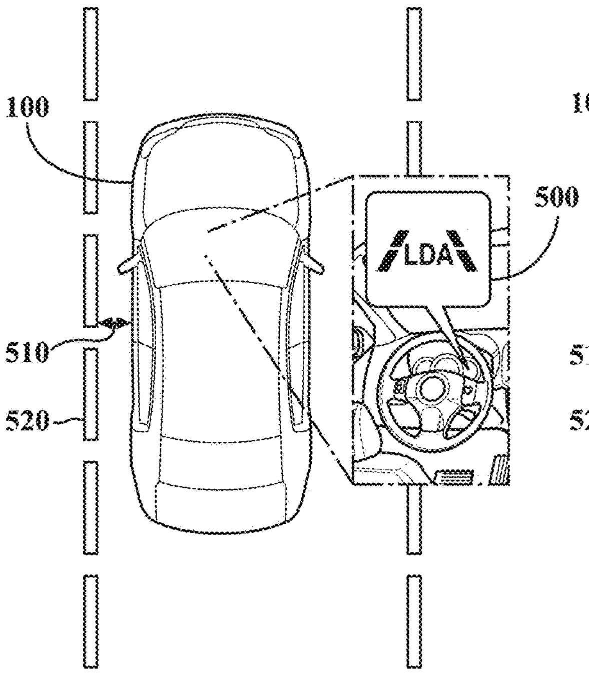
FIGS. 5A and 5B illustrate an example of modifying a lane departure warning signal displayed by a vehicle based on a detected gaze of a driver of the vehicle.
Figure 5B:
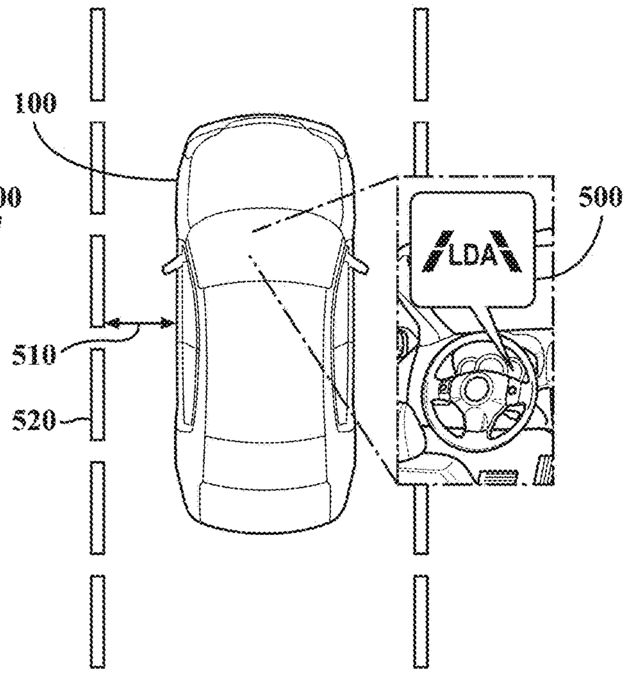

Referring now to FIGS. 5A and 5B, the warning system control module 200 may include instructions that function to control the processor 210 to modify a lane departure warning 500 emitted by the vehicle 100, as mentioned above. In some instances, the abnormality of the gaze of the driver 300 may cause a loss of peripheral vision, as described above. In such instances, it may be advantageous to increase the sensitivity of the lane departure warning system 146 of the vehicle 100. This may help prevent the driver 300 from driving too close to the lane markers or exiting the lane inadvertently. FIG. 5A illustrates an example of a lane departure warning 500 for a driver with a normal gaze. The lane departure warning system 146 may define a distance threshold 510 to a lane marker 520 that may trigger activation of the lane departure warning 500. FIG. 5B illustrates an example of a lane departure warning 500 for a driver with an abnormal gaze. As shown, the distance threshold 510 to the lane marker 520 has been increased to accommodate a driver's loss of peripheral vision. While FIGS. 5A and 5B illustrate examples of lane departure warnings 500 related to the driver's side lane markers, the lane departure warnings 500 related to the passenger's side lane markers may also be modified.

Figure 6A:
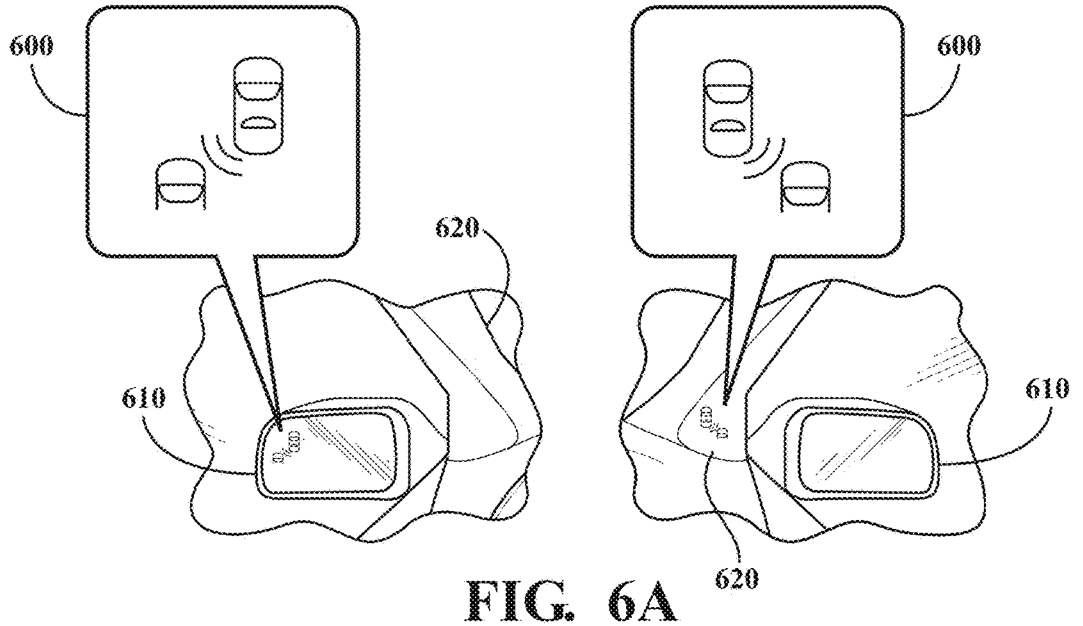
FIGS. 6A and 6B illustrate an example of modifying a blind spot warning signal displayed by a vehicle based on a detected gaze of a driver of the vehicle.
Figure 6B:
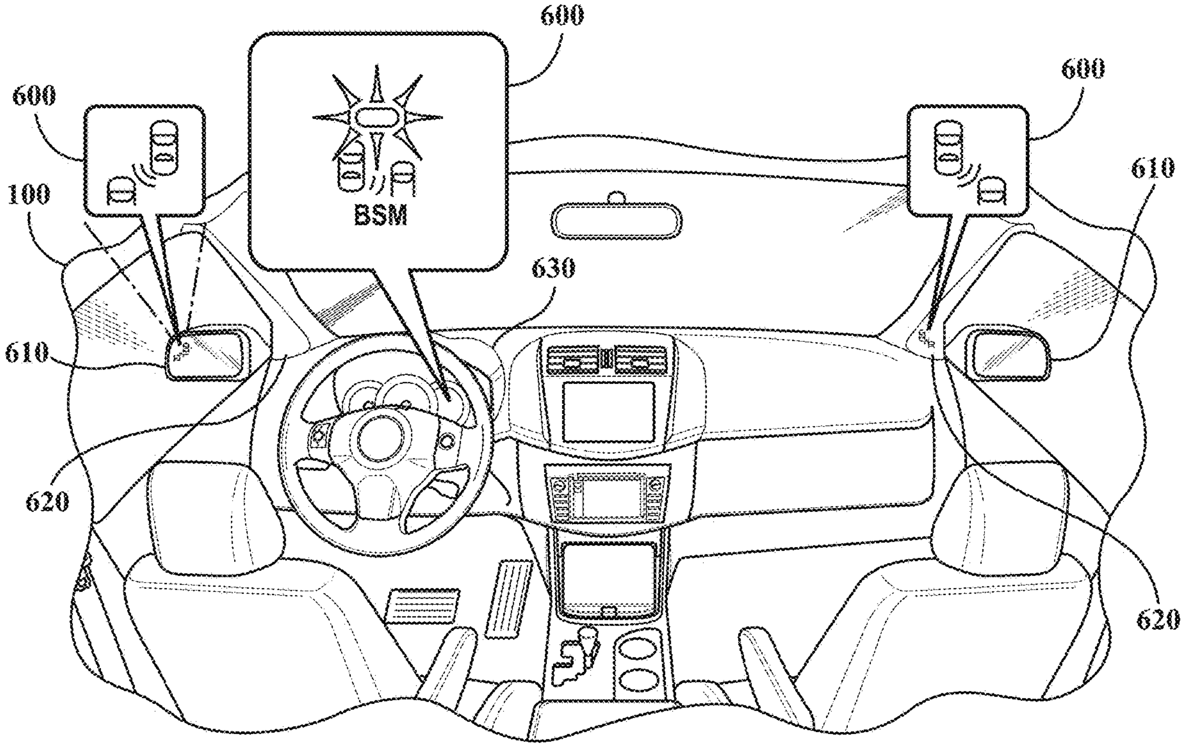

Referring now to FIGS. 6A and 6B, the warning system control module 200 may include instructions that function to control the processor 210 to modify a blind spot warning emitted by the vehicle 100, as mentioned above. In some instances, the abnormality of the gaze of the driver 300 may cause a loss of peripheral vision, as described above. In such instances, it may be advantageous to reposition various signals emitted by the vehicle 100 so that the signals are within the driver's vision. FIG. 6A illustrates examples of conventional blind spot warnings 600 that may be emitted by a vehicle. In many instances, conventional blind spot warnings 600 are emitted by the vehicle on a side view mirror 610 of the vehicle or in a location adjacent the side view mirror such as on the A-pillar 620. FIG. 6B illustrates examples of blind spot warnings 600 for a driver with an abnormal gaze. In some instances, the blind spot warning 600 may be repositioned from the side view mirror 610 and/or the A-pillar 620 to a more central location within the vehicle 100. For example, the blind spot warning 600 may be displaced on a dashboard 630 of the vehicle 100. Other central locations for the blind spot warning 600 include an instrument panel and/or a heads-up display of the vehicle 100. In other instances, the blind spot warning 600 may be displayed in one or more locations in and/or on the vehicle 100. For example, the blind spot warning 600 may be displayed by one or both of the side view mirrors 610, one or both of the A-pillars 620, and the dashboard 630. In some instances, as described above, the processor 210 may determine which eye of the driver is the dominant eye. Based on the location of the dominant eye, the processor 210 can determine the best location in and/or on the vehicle 100 to display the blind spot warning 600. For example, if the right eye of the driver 300 is the dominant eye, the processor 210 can display the blind spot warning 600 on the side view mirror 610 and/or the A-pillar 620 on the right-hand side of the vehicle 100 and/or the dashboard 630 or any other central location within the vehicle 100. If the left eye of the driver 300 is the dominant eye, the processor 210 can display the blind spot warning 600 on the side view mirror 610 and/or the A-pillar 620 on the left-hand side of the vehicle 100, and/or the dashboard 630 or any other central location within the vehicle 100.

In addition to modifying the sensitivity of the warning system and/or repositioning the warning, the warning system control module 200 may also include instructions that function to control the processor 210 to modify the intensity of the signal. For example, the processor 210 can increase the intensity of the signal. The intensity can include the brightness of the signal when the signal is a visual signal, a volume of the signal when the signal is an audible signal, and a vibration force when the signal is a haptic signal.

Figure 7:
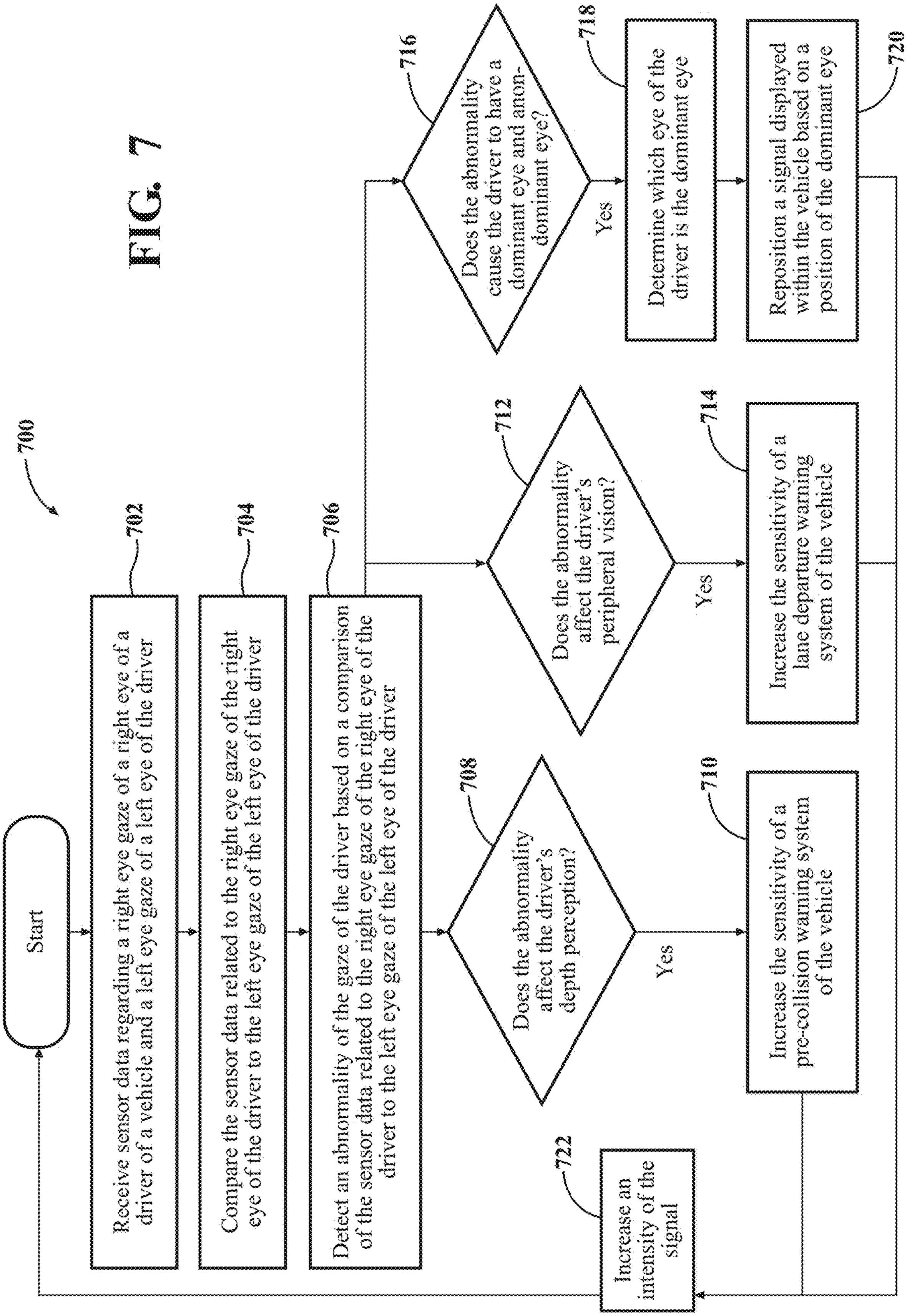
FIG. 7 illustrates a method associated with the warning system control system.

Referring to FIG. 7, a method 700 for controlling a vehicle is shown. The method 700 will be described from the viewpoint of the vehicle 100 of FIG. 1 and the warning system control system 190 of FIG. 2. However, it should be understood that this is just one example of implementing the method 700. While method 700 is discussed in combination with the warning system control system 190, it should be appreciated that the method 700 is not limited to being implemented within the warning system control system 190 but is instead one example of a system that may implement the method 700.

The method 700 may begin at step 702. In step 702, the processor 210 executes instructions stored in the warning system control module 200 that cause the processor 210 to collect and/or receive sensor data 240. The sensor data 240 may include sensor data 140 regarding a right eye gaze of a right eye of a driver 300 of a vehicle 100 and a left eye gaze of a left eye of the driver 300. The sensor data 240 can include information from one or more gaze detector(s) 108 located within a cabin of the vehicle 100. In step 704, the processor 210 executes instructions stored in the warning system control module 200 that cause the processor 210 to compare the sensor data 240 regarding the right eye gaze of the right eye of the driver 300 to the left eye gaze of the left eye of the driver 300. In step 706, the processor 210 executes instructions stored in the warning system control module 200 that cause the processor 210 to detect, based on the comparison performed in step 704, an abnormality of the gaze of the driver 300 based on a comparison of the sensor data 240 related to the right eye gaze of the right eye of the driver 300 to the left eye gaze of the left eye of the driver 300.

In step 708, the processor 210 executes instructions stored in the warning system control module 200 that cause the processor 210 to determine whether the abnormality affects the driver's depth perception. If the processor 210 determines that the abnormality affects the driver's depth perception, the processor 210, in step 710, executes instructions stored in the warning system control module 200 that cause the processor 210 to increase the sensitivity of a pre-collision warning system 144 of the vehicle 100. For example, the processor 210 can increase a distance threshold of the pre-collision warning system 144. An abnormality regarding the driver's depth perception can be determined if the driver has strabismus and/or when the driver's eyes are crossed. As explained previously, the processor 210 using the instructions stored in the warning system control module 200 can compare images captured from the camera(s) 110 to determine if the driver's gaze is crossed, indicating poor depth perception.

In step 712, the processor 210 executes instructions stored in the warning system control module 200 that cause the processor 210 to determine whether the abnormality affects the driver's peripheral vision. If the processor 210 determines that the abnormality affects the driver's peripheral vision, the processor 210, in step 714, executes instructions stored in the warning system control module 200 that cause the processor 210 to increase the sensitivity of a lane departure warning system 146 of the vehicle 100. For example, the processor 210 can increase a distance threshold of the lane departure warning system 146. This type of abnormality can be determined by comparing images captured from the camera(s) 110 to determine if the driver's gaze indicates poor peripheral vision.

In step 716, the processor 210 executes instructions stored in the warning system control module 200 that cause the processor 210 to determine whether the abnormality causes the driver 300 to have a dominant eye and a non-dominant eye. If the processor 210 determines that the abnormality causes the driver 300 to have a dominant eye and a non-dominant eye, the processor 210, in step 718, executes instructions stored in the warning system control module 200 that cause the processor 210 to determine which eye of the driver 300 is the dominant eye.

For example, the processor 210 can determine that the right eye of the driver 300 is the dominant eye, or that the left eye of the driver 300 is the dominant eye. In step 720, the processor 210 executes instructions stored in the warning system control module 200 that cause the processor 210 to reposition a signal displayed within the vehicle 100 based on a position of the dominant eye. For example, if the processor 210 determines that the right eye of the driver 300 is the dominant eye, the processor 210 can reposition a signal displayed within the vehicle 100 to the right side of the vehicle 100 and/or to a central position within the vehicle 100. If the processor 210 determines that the left eye of the driver 300 is the dominant eye, the processor 210 can reposition a signal displayed within the vehicle 100 to the left side of the vehicle 100 and/or to a central position within the vehicle 100.

In step 722, the processor 210 can execute instructions stored in the warning system control module 200 that cause the processor 210 to increase an intensity of the signal. For example, the processor 210 can increase a brightness of a signal when the signal is a visual signal, a volume of the signal when the signal is an audible signal, and a vibration force of the signal when the signal is a haptic signal.

FIG. 1 will now be discussed in full detail as an example environment within which the system and methods disclosed herein may operate. The vehicle 100 can include one or more processor(s) 102. In one or more 102, the processor(s) 102 can be a main processor of the vehicle 100. For instance, the processor(s) 102 can be an electronic control unit (ECU). The vehicle 100 can also include one or more data store(s) 138 for storing one or more types of data. The data store(s) 138 can include volatile and/or non-volatile memory. Examples of data store(s) 138 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store(s) 138 can be a component of the processor(s) 102, or the data store(s) 138 can be operatively connected to the processor(s) 102 for use thereby. The term "operatively connected," as used throughout this description, can include direct or indirect connections, including connections without direct physical contact.

In one or more arrangements, the data store(s) 138 can include sensor data 140. In this context, "sensor data" means any information about the sensors that the vehicle 100 is equipped with, including the capabilities and other information about such sensors. As will be explained below, the vehicle 100 can include the sensor system 104. The sensor data 140 can relate to one or more sensors of the sensor system 104. As an example, in one or more arrangements, the sensor data 140 can include information on one or more LIDAR sensors 116 of the sensor system 104.

In some instances, at least a portion of the sensor data 140 can be located in one or more data stores located onboard the vehicle 100. Alternatively, or in addition, at least a portion of sensor data 140 can be located in one or more data stores that are located remotely from the vehicle 100.

As noted above, the vehicle 100 can include the sensor system 104. The sensor system 104 can include one or more sensors. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process.

In arrangements in which the sensor system 104 includes a plurality of sensors, the sensors can work independently from each other. Alternatively, two or more of the sensors can work in combination with each other. In such a case, the two or more sensors can form a sensor network. The sensor system 104 and/or the one or more sensors can be operatively connected to the processor(s) 102, the data store(s) 138, and/or another element of the vehicle 100 (including any of the elements shown in FIG. 1). The sensor system 104 can acquire data of at least a portion of the external environment of the vehicle 100 (e.g., nearby vehicles).

The sensor system 104 can include any suitable type of sensor. Various examples of different types of sensors will be described herein. However, it will be understood that the embodiments are not limited to the particular sensors described. The sensor system 104 can include one or more vehicle sensor(s) 106. The vehicle sensor(s) 106 can detect, determine, and/or sense information about the vehicle 100 itself. In one or more arrangements, the vehicle sensor(s) 106 can be configured to detect, and/or sense position and orientation changes of the vehicle 100, such as, for example, based on inertial acceleration. In one or more arrangements, the vehicle sensor(s) 106 can include one or more accelerometers, one or more gyroscopes, an inertial measurement unit (IMU), a dead-reckoning system, a global navigation satellite system (GNSS), a global positioning system (GPS), a navigation system 136, and/or other suitable sensors. The vehicle sensor(s) 106 can be configured to detect, and/or sense one or more characteristics of the vehicle 100. In one or more arrangements, the vehicle sensor(s) 106 can include a speedometer to determine a current speed of the vehicle 100.

Additionally or alternatively, the sensor system 104 can include one or more gaze detector(s) 108. The gaze detector(s) 108 can include one or more sensors configured to detect information about a gaze of a driver of the vehicle 100. For example, the gaze detector(s) 108 can be configured to detect a gaze of each eye of the driver in order to determine the gaze of the driver. The gaze detector(s) 108 can include any suitable type of gaze detector(s), for example, one or more camera(s) 110, one or more wearable gaze trackers, etc.

Additionally or alternatively, the sensor system 104 can include one or more environment sensor(s) 112 configured to acquire, and/or sense driving environment data. "Driving environment data" includes data or information about the external environment in which an autonomous vehicle is located or one or more portions thereof. For example, the environment sensor(s) 112 can be configured to detect, quantify and/or sense obstacles in at least a portion of the external environment of the vehicle 100 and/or information/data about such obstacles. Such obstacles may be stationary objects and/or dynamic objects. The environment sensor(s) 112 can be configured to detect, measure, quantify and/or sense other things in the external environment of the vehicle 100, such as, for example, lane markers, signs, traffic lights, traffic signs, lane lines, crosswalks, curbs proximate the vehicle 100, off-road objects, etc.

Various examples of sensors of the sensor system 104 will be described herein. The example sensors may be part of the environment sensor(s) 112 and/or the one or more vehicle sensor(s) 106. However, it will be understood that the embodiments are not limited to the particular sensors described.

As an example, in one or more arrangements, the sensor system 104 can include one or more RADAR sensors 114, one or more LIDAR sensors 116, one or more sonar sensors 118, and/or one or more camera(s) 120. In one or more arrangements, the camera(s) 120 can be high dynamic range (HDR) cameras or infrared (IR) cameras.

The vehicle 100 can also include one or more vehicle system(s) 122. Various examples of the vehicle system(s) 122 are shown in FIG. 1. However, the vehicle 100 can include more, fewer, or different vehicle systems. It should be appreciated that although particular vehicle systems are separately defined, each or any of the systems or portions thereof may be otherwise combined or segregated via hardware and/or software within the vehicle 100. The vehicle 100 can include a propulsion system 124, a braking system 126, a steering system 128, throttle system 130, a transmission system 132, a signaling system 134, and/or a navigation system 136. Each of these systems can include one or more devices, components, and/or a combination thereof, now known or later developed.

The navigation system 136 can include one or more devices, applications, and/or combinations thereof, now known or later developed, configured to determine the geographic location of the vehicle 100 and/or to determine a travel route for the vehicle 100. The navigation system 136 can include one or more mapping applications to determine a travel route for the vehicle 100. The navigation system 136 can include a global positioning system, a local positioning system or a geolocation system.

The vehicle 100 can also include a warning system 142. The warning system 142 is configured to display various signals and/or warnings in or on the vehicle 100 based on information obtained by the sensor system 104. The warning system 142 can include a pre-collision warning system 144. The pre-collision warning system 144 is configured to display a pre-collision warning in and/or on the vehicle 100 when the processor(s) 102 determine, using information obtained by the sensor system 104, that the vehicle 100 may encounter an imminent collision with a preceding vehicle, obstacle, pedestrian, or bicyclist. The warning system 142 can also include a lane departure warning system 146. The lane departure warning system 146 is configured to display a lane departure warning in and/or on the vehicle 100 when the processor(s) 102 determine, using information obtained by the sensor system 104, that the vehicle 100 is nearing a lane marker or crossing a lane marker into an adjacent lane. The warning system 142 can also include a blind spot warning system 148. The blind spot warning system 148 is configured to display a blind spot warning in and/or on the vehicle 100 when the processor(s) 102 determine, using information obtained by the sensor system 104, that there is another vehicle located in a blind spot of the vehicle 100.

The vehicle 100 can also include an input system 150. An "input system" includes any device, component, system, element or arrangement or groups thereof that enable information/data to be entered into a machine. The input system 150 can receive an input from a vehicle passenger (e.g., a driver or a passenger). The vehicle 100 can include an output system 160. An "output system" includes any device, component, or arrangement or groups thereof that enable information/data to be presented to a vehicle passenger (e.g., a person, a vehicle passenger, etc.).

The vehicle 100 can include one or more actuator(s) 170. The actuator(s) 170 can be any element or combination of elements operable to modify, adjust and/or alter one or more of the vehicle system(s) 122 or components thereof to responsive to receiving signals or other inputs from the processor(s) 102 and/or the autonomous driving system 180. Any suitable actuator can be used. For instance, the one or more actuator(s) 170 can include motors, pneumatic actuators, hydraulic pistons, relays, solenoids, and/or piezoelectric actuators, just to name a few possibilities.

The vehicle 100 can include one or more modules, at least some of which are described herein. The modules can be implemented as computer-readable program code that, when executed by a processor, implement one or more of the various processes described herein. One or more of the modules can be a component of the processor(s) 102, or one or more of the modules can be executed on and/or distributed among other processing systems to which the processor(s) 102 are operatively connected. The modules can include instructions (e.g., program logic) executable by one or more processor(s) 102. Additionally or alternatively, the data store(s) 138 may contain such instructions.

In one or more arrangements, one or more of the modules described herein can include artificial or computational intelligence elements, e.g., neural network, fuzzy logic, or other machine learning algorithms. Further, in one or more arrangements, one or more of the modules can be distributed among a plurality of the modules described herein. In one or more arrangements, two or more of the modules described herein can be combined into a single module.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-7, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Generally, module as used herein includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™ Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC, or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A system comprising:

a processor; and a memory in communication with the processor, the memory having a warning system module having instructions that, when executed by the processor, cause the processor to:

receive sensor data regarding a right eye gaze of a right eye of a driver of a vehicle and a left eye gaze of a left eye of the driver;

compare the sensor data related to the right eye gaze of the right eye of the driver to the left eye gaze of the left eye of the driver;

detect an abnormality of a gaze of the driver based on a comparison of the sensor data related to the right eye gaze of the right eye of the driver to the left eye gaze of the left eye of the driver; and modify, using the sensor data, a signal emitted by the vehicle when the abnormality is detected.

2. The system of claim 1, wherein the abnormality is caused by at least one of amblyopia, strabismus, a loss of depth perception, and an optical prosthesis.

3. The system of claim 1, wherein modifying the signal includes increasing, by the processor, a sensitivity of a warning system that emits the signal, wherein the sensitivity of the warning system is a distance threshold, and wherein the warning system is at least one of a pre-collision warning system and a lane departure warning system.

4. The system of claim 1, wherein the instructions further cause the processor to:

determine which eye of the driver is a dominant eye of the driver, wherein modifying the signal includes repositioning, by the processor, the signal displayed by the vehicle based on a position of the dominant eye, the signal being a visual signal.

5. The system of claim 4, wherein repositioning the signal includes displaying the visual signal on a central location within the vehicle when an unmodified position of the visual signal is located adjacent to an external mirror being on a side of the vehicle opposite the dominant eye.

6. The system of claim 1, wherein modifying the signal includes increasing, by the processor, an intensity of the signal, wherein the intensity includes at least one of a brightness of a signal when the signal is a visual signal, a volume of the signal when the signal is an audible signal, and a vibration force of the signal when the signal is a haptic signal.

7. A method comprising steps of:

detecting, using a processor including sensor data having information about a gaze of each eye of a driver of a vehicle, an abnormality of a gaze of the driver, wherein the abnormality is caused by at least one of amblyopia, strabismus, a loss of depth perception, and an optical prosthesis; and modifying, using the processor, a signal emitted by the vehicle when the abnormality is detected.

8. The method of claim 7, further comprising steps of:

receiving, by the processor, sensor data regarding a right eye gaze of a right eye of the driver and a left eye gaze of a left eye of the driver;

comparing, by the processor, the sensor data related to the right eye gaze of the right eye of the driver to the left eye gaze of the left eye of the driver; and detecting, by the processor, the abnormality based on a comparison of the sensor data related to the right eye gaze of the right eye of the driver to the left eye gaze of the left eye of the driver.

9. The method of claim 7, wherein the step of modifying the signal further includes the step of increasing, by the processor, a sensitivity of a warning system that emits the signal, wherein the sensitivity of the warning system is a distance threshold, and wherein the warning system is at least one of a pre-collision warning system and a lane departure warning system.

10. The method of claim 7, further comprising steps of:

determining, by the processor, which eye of the driver is a dominant eye of the driver, wherein the step of modifying the signal further includes the step of repositioning, by the processor, the signal displayed by the vehicle based on a position of the dominant eye, the signal being a visual signal.

11. The method of claim 9, wherein the signal is a visual signal, and wherein the step of repositioning the signal further includes the step of:

displaying the visual signal on a central location within the vehicle when an unmodified position of the visual signal is located adjacent to an external mirror being on a side of the vehicle opposite a dominant eye of the driver.

12. The method of claim 7, wherein the step of modifying the signal includes the step of increasing, by the processor, an intensity of the signal, wherein the intensity includes at least one of a brightness of a signal when the signal is a visual signal, a volume of the signal when the signal is an audible signal, and a vibration force of the signal when the signal is a haptic signal.

13. A non-transitory computer-readable medium including instructions that, when executed by a processor, cause the processor to:

receive sensor data regarding a right eye gaze of a right eye of a driver of a vehicle and a left eye gaze of a left eye of the driver;

compare the sensor data related to the right eye gaze of the right eye of the driver to the left eye gaze of the left eye of the driver;

detect an abnormality of a gaze of the driver based on a comparison of the sensor data related to the right eye gaze of the right eye of the driver to the left eye gaze of the left eye of the driver; and modify, using the sensor data, a signal emitted by the vehicle when the abnormality is detected.

14. The non-transitory computer-readable medium of claim 13, wherein the abnormality is caused by at least one of amblyopia, strabismus, a loss of depth perception, and an optical prosthesis.

15. The non-transitory computer-readable medium of claim 13, wherein modifying the signal includes increasing, by the processor, a sensitivity of a warning system that emits the signal, wherein the sensitivity of the warning system is a distance threshold, and wherein the warning system is at least one of a pre-collision warning system and a lane departure warning system.

16. The non-transitory computer-readable medium of claim 13, wherein the instructions further cause the processor to determine which eye of the driver is a dominant eye of the driver, and wherein modifying the signal includes repositioning, by the processor, the signal by the vehicle based on a position of the dominant eye, the signal being a visual signal.

17. The non-transitory computer-readable medium of claim 16, wherein repositioning the signal includes displaying the visual signal on a central location within the vehicle when an unmodified position of the visual signal is located adjacent to an external mirror being on a side of the vehicle opposite the dominant eye.

* * * * *